US010731126B2

(12) United States Patent
Sieck et al.

(10) Patent No.: US 10,731,126 B2
(45) Date of Patent: Aug. 4, 2020

(54) DEEP EUTECTIC SOLVENTS AND/OR IONIC LIQUIDS IN CELL CULTURE MEDIA

(71) Applicant: Merck Patent GmbH, Darmstadt (DE)

(72) Inventors: Jochen Bastian Sieck, Darmstadt (DE); Michael Howard Rayner, Seeheim-Jugenheim (DE); Joerg Von Hagen, Pfungstadt (DE); Claudia Knack, Darmstadt (DE)

(73) Assignee: Merck Patent GmbH, Darmstadt (DE)

( * ) Notice: Subject to any disclaimer, the term of this patent is extended or adjusted under 35 U.S.C. 154(b) by 52 days.

(21) Appl. No.: 15/577,376

(22) PCT Filed: May 2, 2016

(86) PCT No.: PCT/EP2016/000717
§ 371 (c)(1),
(2) Date: Nov. 28, 2017

(87) PCT Pub. No.: WO2016/192830
PCT Pub. Date: Dec. 8, 2016

(65) Prior Publication Data
US 2018/0163171 A1    Jun. 14, 2018

(30) Foreign Application Priority Data

May 29, 2015  (EP) ..................... 15001613

(51) Int. Cl.
*C12N 5/00*  (2006.01)
(52) U.S. Cl.
CPC ........ *C12N 5/0018* (2013.01); *C12N 2500/33* (2013.01); *C12N 2500/38* (2013.01); *C12N 2500/46* (2013.01); *C12N 2500/60* (2013.01); *C12N 2510/02* (2013.01)
(58) Field of Classification Search
None
See application file for complete search history.

(56) References Cited

U.S. PATENT DOCUMENTS

| | | | | |
|---|---|---|---|---|
| 5,122,469 | A * | 6/1992 | Mather | C12N 5/0037 435/383 |
| 9,243,224 | B2 | 1/2016 | Budach | |

FOREIGN PATENT DOCUMENTS

| | | |
|---|---|---|
| EP | 1805131 B1 | 2/2011 |
| WO | 2004063383 A1 | 7/2004 |
| WO | 2006038013 A2 | 4/2006 |
| WO | 2007036712 A1 | 4/2007 |
| WO | 2007063327 A1 | 6/2007 |
| WO | 2011015589 A1 | 2/2011 |
| WO | 2011134921 A1 | 11/2011 |

OTHER PUBLICATIONS

Hayyan, M. et al. Feb. 2015 In vitro and in vivo toxicity profiling of ammonium-based deep eutectic solvents. PLoS One 10(2): 1-18. specif. pp. 1, 3.*
Paiva, A. et al. Mar. 2014. Natural deep eutectic solvents—solvents for the 21st century. ACS Sustainable Chemistry & Engineering 2: 1063-1071. specif. pp. 1063, 1064, 1066, 1067.*
Human Metabolome Database (HMDB). Choline. Datasheet [online]. HMDB0000097. [retrieved on Aug. 1, 2019]. Retrieved from the Internet: <URL: http://www.hmdb.ca/metabolites/HMDB0000097> pp. 1 and 2.*
Grauffel, C. et al. 2013. Cation-pi interactions as lipid-specific anchors for phosphatidylinositol-specific phospholipase C. Journal of the American Chemical Society 135: 5740-5750. specif. pp. 5740, 5744.*
Gutierrez, M.C. et al. 2010. Bacteria incorporation in deep-eutectic solvents through freeze-drying. Angewandte Chemie Int. Ed. 49: 2158-2162. specif. pp. 2158, 2160, 2161.*
Serva Electrophoresis. 2007. M9 Minimal Salts 5x, Powder. Cat. No. 48505. Instruction Manual. [retrieved on Aug. 2, 2019]. Retrieved from the Internet: <URL: https://www.serva.de/www_root/documents/48505_e.pdf>. p. 1.*
International Search Report PCT/EP2016/000717 dated Jul. 28, 2016.
Mann Hayyan et al: "In Vitro and In Vivo Toxicity Profiling of Ammonium-Based Deep Eutectic Solvents", PLOS ONE, vol. 10, No. 2, Feb. 13, 2015 (Feb. 13, 2015), pp. e0117934, XP055286119, DOI: 10.1371/journal.pone.0117934.
Yuntao Dai et al: "Natural deep eutectic solvents as new potential media for green technology", Analytica Chimica Acta, vol. 766, Mar. 1, 2013 (Mar. 1, 2013), NL, pp. 61-68, XP055286799, ISSN: 0003-2670, DOI: 10.1016/j.aca.2012.12.019.
V. Fischer: "Properties and Applications of Deep Eutectic Solvents and Low-Melting Mixtures", Apr. 24, 2015 (Apr. 24, 2015), XP055287000, Retrieved from the Internet [retrieved on Jul. 8, 2015].
Venkata Nancharaiah Y et al: "Alkyl-methylimidazolium ionic liquids affect the growth and fermentative metabolism ofsp", Bioresource Technology, Elsevier BV, GB, vol. 102, No. 11, Mar. 16, 2011 (Mar. 16, 2011), pp. 6573-6578, XP028480911, ISSN: 0960-8524, [retrieved on Mar. 21, 2011], DOI: 10.1016/J.BIORTECH.2011.03.042.
Nancharaiah Y V et al: "Hormetic effect of ionic liquid 1-ethyl-3-methylimidazolium acetate on bacteria", Chemosphere, vol. 128, Feb. 19, 2015 (Feb. 19, 2015), pp. 178-183, XP029148033, ISSN: 0045-6535, DOI: 10.1016/J.CHEMOSPHERE.2015.01.032.
Ronja Mueller et al: "Improved fed-batch bioprocesses using chemically modified amino acids in concentrated feeds", BMC Proceedings, Biomed Central LTD, London UK, vol. 7, No. Suppl 6, Dec. 4, 2013 (Dec. 4, 2013), pp. P46, XP021170344, ISSN: 1753-6561, DOI: 10.1186/1753-6561-7-S6-P46.
Claudia Knack et al: "Manufacturing ultra-concentrated liquid feeds: Transitioning the aqueous solubility barrier of the feed amino acids cysteine and tyrosine", BMC Proceedings, vol. 9, No. Suppl 9, Dec. 14, 2015 (Dec. 14, 2015), London UK, pp. P54, XP055286191, ISSN: 1753-6561, DOI: 10.1186/1753-6561-9-S9-P54.

(Continued)

*Primary Examiner* — Thomas J. Visone
*Assistant Examiner* — Sharon M. Papciak
(74) *Attorney, Agent, or Firm* — Millen White Zelano and Branigan, PC; Csaba Henter

(57) ABSTRACT

The present invention relates to cell culture media compositions comprising deep eutectic solvents and/or ionic liquids.

17 Claims, 6 Drawing Sheets

(56) References Cited

OTHER PUBLICATIONS

R. Sheldon, "Catalytic reactions in ionic liquids", Chern. Comm, 2001, 2399-2407.
Earle M.J. and Seddon K.R. "Ionic liquids. Green solvents for the future", Pure Appl. Chern., vol. 72, No. 7, 2000, 1391-1398.
T. Welton, ,Room-Temperature Ionic Liquids. Solvents for Synthesis and Catalysis, Chern. Rev. 1999, 99, 2071-2083.
Hagiwara R, Ito Y., Room temperature ionic liquids of alkylimidazolium cations and fluoroanions, Journal of Fluorine Chemistry, 105, 2000, 221-227.
Zhang Q. et al., "Deep eutectic solvents: synthesis, properties and appilcations" Chern. Soc. Rev., 2012, 41, 7108-7146.
Abbott A. P. et al, "Deep Eutectic Solvents Formed between Choline Choride and Carboxylic Acids: Versatile Alternatives to ionic Liquids", J. Am. Chern. Soc., 2004, 126, 9142-9147.
Wasserscheid P. and Welton T. (Eds.) ,Ionic Liquieds in Synthesis, Second Edtion, Wiley,VCH, 2008.

\* cited by examiner

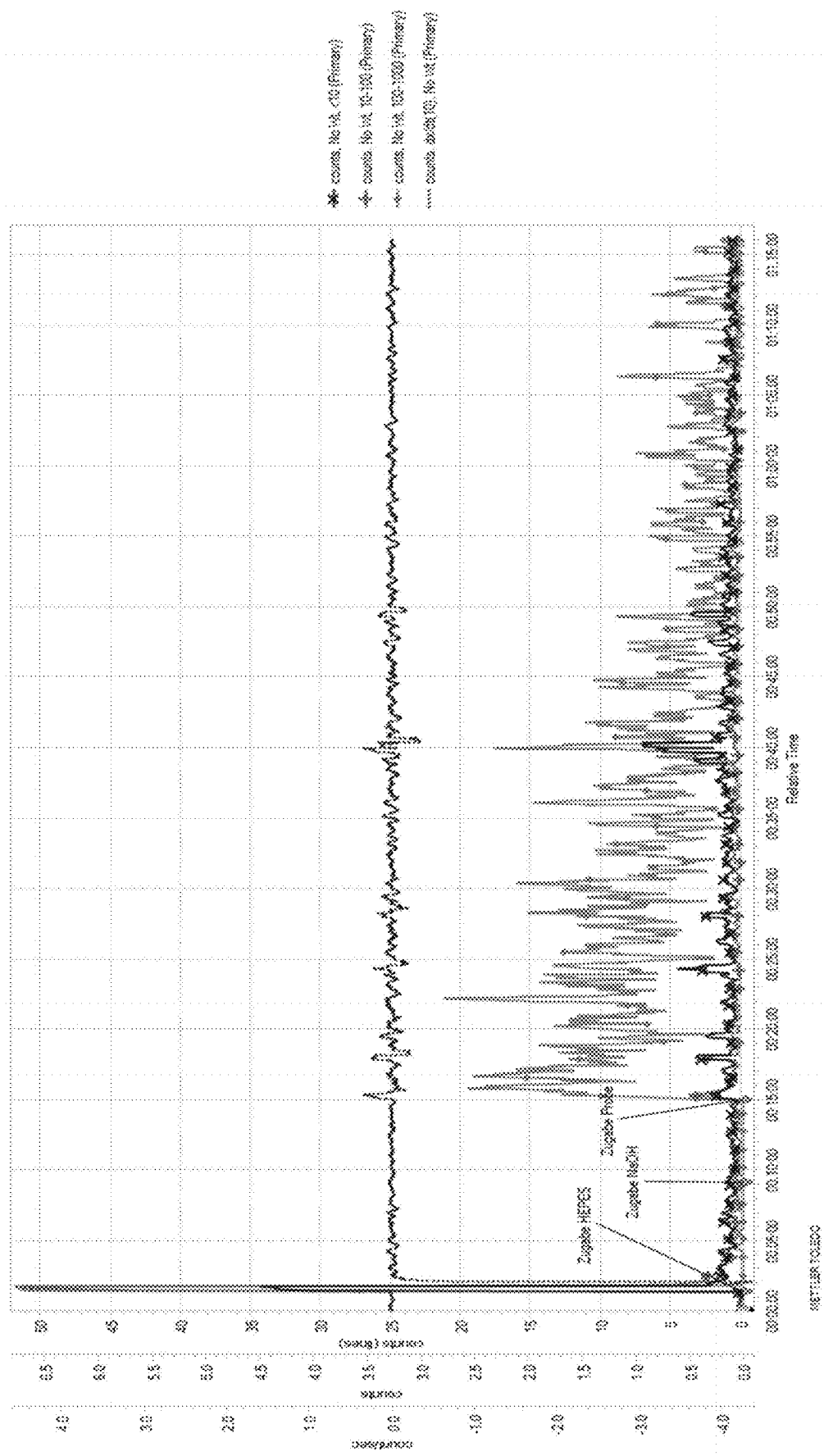
Fig. 1 - Powder

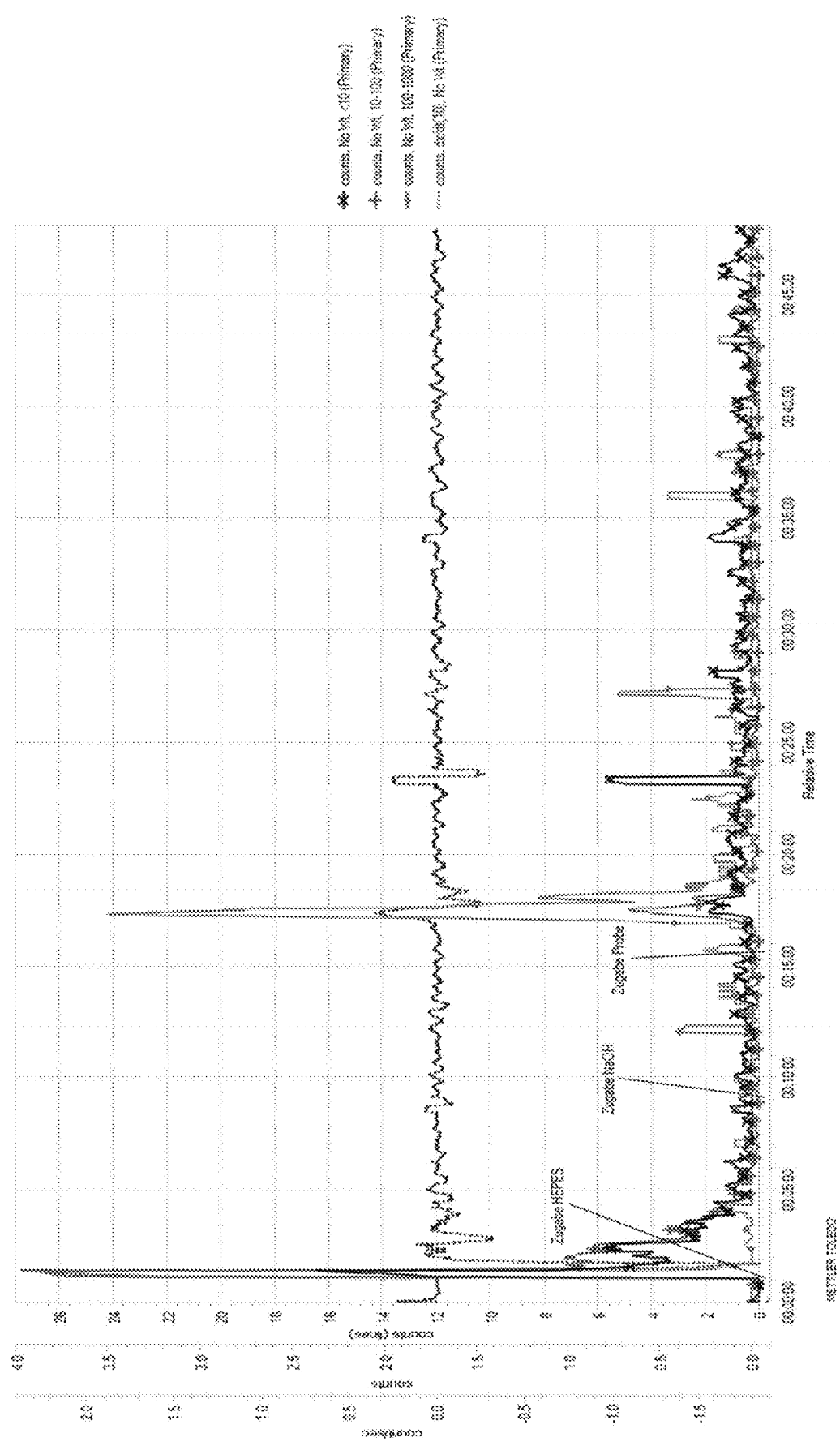
Fig. 2 - DES

DEEP EUTECTIC SOLVENTS AND/OR IONIC LIQUIDS IN CELL CULTURE MEDIA

The present invention relates to cell culture media comprising deep eutectic solvents and/or ionic liquids.

Cell culture media in aqueous solution can provide an environment which supports and maintains the growth of cells and/or maintains a desired physiological cellular condition adventitious to the targeted production of certain products, so called target molecules.

Cell culture media comprise of a complex mixture of components, sometimes more than one hundred different components, depending on the type of organism whose growth and/or targeted physiological status shall be supported.

The first cell culture media that were developed were complex media consisting of diverse mixtures of components which were very poorly chemically defined, poorly characterized and difficult to manufacture with a consistent quality, such as plasma, serum, embryo extracts, and/or other biological extracts or peptones. A major advance was thus made with the development of chemically defined media. Chemically defined media often comprise of, but are not exclusively limited to, amino acids, vitamins, saccharides, metal salts, antioxidants, chelators, growth factors, buffers, hormones, and many more substances known to those expert in the art.

Some cell culture media are offered as sterile aqueous liquids. The disadvantage of liquid cell culture media is their reduced shelf life and difficulties for shipping and storage. As a consequence, many cell culture media are presently offered as finely milled dry powder mixtures. These are designed, often with other supplements, for supplying cells with a substantial nutrient base for growth and/or production of biopharmaceuticals from said cells and/or used as a feed to supply cells when specific nutrients are used up.

For the final use in cell culture, the dry powder mixtures are dissolved in water and/or aqueous solutions and are added to the cell culture in the dissolved state because it is typically desirable to have components for use in cell culture in a liquid form due to the inherent disadvantages of solids, for example difficulty of sterile addition and/or turbidity of solids added due to slow dissolution. In addition, solids are more difficult to dose to systems, for example to bioreactor systems containing biological entities.

Often the pure nutrient components are solids in and around room temperature. Consequently, such components need to be dissolved in solvents in order to provide a practicable liquid form. This has the disadvantage, for many poorly soluble components, that large volumes are required to add the desired component.

Therefore, it would be favourable to find a way to provide cell culture media in a form that has a long shelf life like dry powder mixtures but which at the same time dissolve easily in solvents like water without getting too diluted.

It has been found that deep eutectic solvents and/or ionic liquids can be used as highly concentrated media components for cell culture in bioreactors. Deep eutectic solvents and/or ionic liquids have a long shelf life, are per se liquid and do not need to be dissolved by the addition of a solvent which has no other effect on the cell culture than diluting it. At least one component of the deep eutectic solvent and/or ionic liquid is, favourably, a nutrient component which is needed to supply the cells in culture.

The present invention is thus directed to a cell culture medium composition or kit comprising a dry cell culture medium and a liquid cell culture medium comprising a deep eutectic solvent and/or an ionic liquid. That means the cell culture medium composition comprises at least two components a dry one and a liquid one.

In a preferred embodiment, the cell culture medium composition is a base medium or a feed medium.

In a preferred embodiment, the liquid cell culture medium of the cell culture medium composition is liquid at or below 100° C., preferably at or below 50° C., most preferred it is liquid at or below 35° C., especially between 20 and 35° C. In any case it is added to the bioreactor in which the cell culture is performed in the liquid state, that means at a temperature at which it is liquid.

In a preferred embodiment, the liquid cell culture medium comprises a deep eutectic solvent.

In another preferred embodiment, the liquid cell culture medium comprises a quaternary ammonium salt. The quaternary ammonium salt is typically a part of the deep eutectic solvent.

In a very preferred embodiment, the liquid cell culture medium comprises choline and/or betaine. The choline and/or betaine is typically a part of the deep eutectic solvent.

In another embodiment, the liquid cell culture medium comprises amino acids, preferably cysteine and/or tyrosine. The amino acids are typically a part of the deep eutectic solvent.

In another embodiment, the liquid cell culture medium comprises other components which are not part of the ionic liquid or deep eutectic solvent and which are dissolved in the ionic liquid and/or deep eutectic solvent.

The present invention is further directed to a process for cell culture comprising the following steps:
a) Providing a bioreactor and a cell culture media composition according to the present invention
b) Dissolving the cell culture media composition in a solvent to generate a liquid cell culture medium
c) Adding to the bioreactor the liquid cell culture medium of step b) either as a base medium to which the cells to be cultured are added afterwards or as a feed medium which is added to cells already present in a liquid medium within the bioreactor
d) Performing cell culture in said bioreactor. This is typically done by incubating the cells under suitable conditions like pH, osmolality, temperature, agitation, aeration (oxygen/$CO_2$) etc. and the optional addition of feed medium one or several times during the cell culture.

In a preferred embodiment, the cell culture media composition of step a) comprises a liquid cell culture medium that is liquid at a temperature between 20 and 35° C.

In another embodiment, the cell culture media composition of step a) comprises a liquid cell culture medium that comprises amino acids, preferably cysteine and/or tyrosine.

In one embodiment, the cells added to the bioreactor in step c) are stem cells, eukaryotic cells, prokaryotic cells, archaea, bacteria, yeasts, fungi, insect cells or algae.

In one embodiment, the cell culture media composition of step a) comprises a liquid cell culture medium that comprises less than 50% (w/w), preferably less than 20% of water, most preferred less than 10% of water.

FIGS. 1 to 5 show a comparison between the dissolution of a dry powder tyrosine HCl sample and a DES comprising tyrosine HCl. Further details can be found in Example 1.

A cell culture is any setup in which cells are cultured. A cell culture is for example used to e.g. produce cells (such as stem cells or cellular compartments), or to produce target molecules like pharmaceuticals, recombinant proteins, viruses, vaccines, enzymes, metabolites, hormones, lipids, colour agents, nucleic acids, etc.

A cell culture is performed in a bioreactor. A bioreactor is any unit suitable for the culture of cells, such as a container, vessel, bag, flask, fermenter or tank in which cells can be cultured. A bioreactor is typically sterilized prior to use. Incubation is typically performed under suitable conditions such as suitable temperature, osmolality, aeration, agitation, etc. A person skilled in the art is aware of suitable incubation conditions for supporting or maintaining the growth/culturing of cells.

A cell culture medium according to the present invention is any mixture of components which maintains and/or supports the in vitro growth of cells and/or supports a particular physiological state. It might be a complex medium or a chemically defined medium. A cell culture medium can comprise all components necessary to maintain and/or support the in vitro growth of cells or be used for the addition of selected components in combination with further components that are added separately. Examples of cell culture media according to the present invention are full media, also called base media, which comprise all components necessary to maintain and/or support the in vitro growth of cells as well as media supplements or feed media.

Typically, the cell culture media according to the invention are used to maintain and/or support the growth of cells and/or support a particular physiological state in a bioreactor.

During the growth of cells in a bioreactor or fermenter it is often economically important to maintain the growth phase and/or the production phase on-going for a long period of time (days, weeks, months). Thus, often, some initial components supplied to the cells as base medium become exhausted. Such components cannot always be supplied initially at higher concentration due to solubility problems and/or because they have a toxic and/or otherwise negative effect on the manufacturing process. Thus, such components need to be added later either continuously or discontinuously during the running axenic culturing process into the bioreactor. Such components are, for example cysteine, or it's biologically relevant and/or active derivatives as well as tyrosine since they are essential to many cells and/or manufacturing processes.

A feed medium is thus a cell culture medium that is added to a cell culture continuously or discontinuously at a later stage of the cell culture process. That means it is not the cell culture base medium with which the cells are mixed to start the cell culture process in the bioreactor. A feed medium is typically added to a bioreactor one or several times in the course of the process. A feed medium is typically added as a nutrient feed and/or as an osmolarity modulator and/or as a pH regulator and/or to support growth of cells and/or to support the production of target molecules.

A feed medium typically comprises less components than a full medium. It may only comprise one or two components. Typically it comprises 2 to 50, preferably 2 to 10 components.

The cell culture media according to the present invention can be designed to be suitable to grow or maintain/support the growth many different kinds of organism, e.g. prokaryotic cells like bacterial cells or eukaryotic cells like yeast, fungi, algae, plant, insect or mammalian cells or archaea. The cells can be normal cells, immortalized cells, diseased cells, transformed cells, mutant cells, somatic cells, germ cells, stem cells, precursor cells or embryonic cells, any of which may be established or transformed cell lines or obtained from natural sources.

A mammalian cell culture medium is a mixture of components which maintain and/or support the in vitro growth of mammalian cells. Examples of mammalian cells are human or animal cells, preferably CHO cells, COS cells, I VERO cells, BHK cells, AK-1 cells, SP2/0 cells, L5.1 cells, hybridoma cells, insect cells or human cells.

Preferably the cell culture media according to the present invention, are chemically defined cell culture media.

Chemically defined cell culture media are cell culture media comprising of chemically well characterized 'defined' raw materials. This means that the chemical composition of all the chemicals used in the media is known. The chemically defined media do not comprise of chemically ill-defined yeast, animal or plant tissues; they do not comprise feeder cells, serum, extracts or digests or other components which may contribute chemically poorly defined proteins and/or peptides and/or hydrolysates to the media. Chemically undefined or poorly defined chemical components are those whose chemical composition and structure is not well known, are present in poorly defined and varying composition or could only be defined with enormous experimental effort—comparable to the evaluation of the chemical composition and structure of a protein-digest from albumin or casein.

A powdered cell culture medium or a dry powder medium is a cell culture medium typically resulting from a milling process or a lyophilisation process.

That means the powdered cell culture medium is typically a finely granular, particulate medium—not a liquid medium. The term "dry powder" may be used interchangeably with the term "powder;" however, "dry powder" as used herein simply refers to the gross appearance of the granulated material and is not intended to mean that the material is completely free of complexed or agglomerated solvent unless otherwise indicated. A powdered cell culture medium can also be a granulated cell culture medium, e.g. dry granulated by roller compaction.

A full cell culture medium to be used in the process of the present invention typically comprises at least one or more saccharide components, one or more amino acids, one or more vitamins or vitamin precursors, one or more salts, one or more buffer components, one or more co-factors and one or more nucleic acid components. It may also comprise recombinant proteins, e.g. rinsulin, rBSA, rTransferrin, rCytokines etc.

The media may also comprise sodium pyruvate, vegetable proteins, digests or extracts, fatty acids and/or fatty acid derivatives and/or pluronic product components (block copolymers based on ethylene oxide and propylene oxide) in particular Poloxamer 188 sometimes called Pluronic F 68 or Kolliphor P 188 or Lutrol F 68 and/or surface active components such as chemically prepared non-ionic surfactants. One example of a suitable non-ionic surfactant are difunctional block copolymer surfactants terminating in primary hydroxyl groups also called poloxamers, e.g. available under the trade name Pluronic® from BASF, Germany. Such pluronic product components are in the following just called pluronic.

Saccharide components are all mono- or di-saccharides, like glucose, galactose, ribose or fructose (examples of monosaccharides) or sucrose, lactose or maltose (examples of disaccharides). Saccharide components may also be oligo- or polysaccharides.

Examples of amino acids according to the invention are the proteinogenic amino acids, especially the essential amino acids, leucine, isoleucine, lysine, methionine, phenylalanine, threonine, tryptophan and valine, as well as the non-proteinogenic amino acids such as D-amino acids.

Tyrosine means L- or D-tyrosine, preferably L-tyrosine.
Cysteine means L- or D-cysteine, preferably L-cysteine.
Amino acid precursors and analogues are also included.

Examples of vitamins are Vitamin A (Retinol, retinal, various retinoids, and four carotenoids), Vitamin $B_1$ (Thiamine), Vitamin $B_2$ (Riboflavin), Vitamin $B_3$ (Niacin, niacinamide), Vitamin $B_5$ (Pantothenic acid), Vitamin $B_6$ (Pyridoxine, pyridoxamine, pyridoxal), Vitamin $B_7$ (Biotin), Vitamin $B_9$ (Folic acid, folinic acid), Vitamin $B_{12}$ (Cyanocobalamin, hydroxycobalamin, methylcobalamin), Vitamin C (Ascorbic acid), Vitamin D (Ergocalciferol, cholecalciferol), Vitamin E (Tocopherols, tocotrienols) and Vitamin K (phylloquinone, menaquinones). Vitamin precursors and analogues are also included.

Examples of salts are components comprising inorganic ions such as bicarbonate, calcium, chloride, magnesium, phosphate, potassium and sodium or trace elements such as Co, Cu, F, Fe, Mn, Mo, Ni, Se, Si, Ni, Bi, V and Zn. Examples are copper(II) sulphate pentahydrate ($CuSO_4.5H_2O$), sodium chloride (NaCl), calcium chloride ($CaCl_2.2H_2O$), potassium chloride (KCl), iron(II)sulphate, sodium phosphate monobasic anhydrous ($NaH_2PO_4$), magnesium sulphate anhydrous ($MgSO_4$), sodium phosphate dibasic anhydrous ($Na_2HPO_4$), magnesium chloride hexahydrate ($MgCl_2.6H_2O$), zinc sulphate heptahydrate ($ZnSO_4.7H_2O$).

Examples of buffers are carbonate, phosphate, HEPES, PIPES, ACES, BES, TES, MOPS and TRIS.

Examples of cofactors are thiamine derivatives, biotin, vitamin C, NAD/NADP, cobalamin, vitamin B12, flavin mononucleotide and derivatives, glutathione, heme, nucleotide phophates and derivatives.

Nucleic acid components, according to the present invention, are the nucleobases, like cytosine, guanine, adenine, thymine or uracil, the nucleosides like cytidine, uridine, adenosine, guanosine and thymidine, and the nucleotides such as adenosine monophosphate or adenosine diphosphate or adenosine triphosphate.

Ionic liquids or liquid salts as used in the present invention are ionic species which typically consist of an organic cation and an inorganic or organic anion. They do not contain any neutral molecules and are liquid below 100° C., preferably below 50° C., most preferred below 35° C.

The area of ionic liquids is currently being researched intensively since the potential applications are multifarious. Review articles on ionic liquids are, for example, R. Sheldon "Catalytic reactions in ionic liquids", *Chem. Commun.*, 2001, 2399-2407; M. J. Earle, K. R. Seddon "Ionic liquids. Green solvent for the future", *Pure Appl. Chem.*, 72 (2000), 1391-1398; P. Wasserscheid, W. Keim "Ionische Flüssigkeiten—neue Lösungen für die Übergangsmetallkatalyse" [Ionic Liquids—Novel Solutions for Transition-Metal Catalysis], *Angew. Chem.*, 112 (2000), 3926-3945; T. Welton "Room temperature ionic liquids. Solvents for synthesis and catalysis", *Chem. Rev.*, 92 (1999), 2071-2083 or R. Hagiwara, Ya. Ito "Room temperature ionic liquids of alkylimidazolium cations and fluoroanions", *J. Fluorine Chem.*, 105 (2000), 221-227).

In general, all ionic liquids of the general formula $K^+A^-$ known to the person skilled in the art, in particular those which are miscible with water and non-toxic to the cells to be cultured, that means which are biologically compatible, are suitable in the method according to the invention.

The anion $A^-$ of the ionic liquid is preferably biologically compatible and e.g. selected from the group comprising $OH^-$, halides, borates, phosphates, phosphites, phosphonates, phosphinates, silicates, cyanamide, thiocyanate, anions of carboxylic acids, carbonates, sulfates, sulphites, sulfonates, nitrate ($[NO_3]^-$), anions of organic acids, or imides of the general formula $[N(R_f)_2]^-$ or of the general formula $[N(XR_f)_2]^-$, where $R_f$ denotes partially or fully fluorine-substituted alkyl having 1 to 8 C atoms and X denotes $SO_2$ or CO.

Halides are for example $Cl^-$, $Br^-$, $I^-$, preferably, $Cl^-$, $Br^-$.

Borates are for example $BO_3^{3-}$, $HBO_3^{2-}$, $H_2BO_3^-$, $R_2BO_3^-$, $RHBO_3^{2-}$, $B(OR)(OR)(OR)(OR)^-$, $B(HSO_4)^-$, $B(RSO_4)^-$, $BF_zR^F_{4-z}^-$, with z=0, 1, 2 or 3.

Phosphates are for example $PO_4^{3-}$, $HPO_4^{2-}$, $H_2PO_4^-$, $R_2PO_4^-$, $RPO_4^{2-}$, $HRPO_4^-$, $PR^F_yF_{6-y}^-$, with y=1, 2, 3, 4, 5 or 6.

Phosphites are for example $PO_3^{3-}$, $HPO_3^{2-}$, $H_2PO_3^-$, $R_2PO_3^-$, $RPO_3^{2-}$, $HRPO_3^-$.

Carboxylic acids and carbonates are for example $CH_3COO^-$, $RCOO^-$, $HCO_3^-$, $CO_3^{2-}$, $RCO_3^-$ Sulfates, sulphites, sulfonates are for example $SO_4^{2-}$, $HSO_4^-$, $SO_3^{2-}$, $HSO_3^-$, $ROSO_3^-$, $RSO_3^-$.

Phosphonates and phosphinates are for example $RHPO_3^-$, $R_2PO_2^-$, $R_2PO_3^-$.

Silicates are for example $SiO_4^{4-}$, $HSiO_4^{3-}$, $H_2SiO_4^{2-}$, $R_2SiO_4^{2-}$, $RSiO_4^{3-}$, $R_3SiO_4^-$, $H_2RSiO_4^-$.

In which R is each independently of another a non-fluorinated, partially fluorinated or perfluorinated straight-chain or branched alkyl group having 1 to 6 C atoms.

If R is perfluorinated it is preferably trifluoromethyl, pentafluoroethyl or nonafluorobutyl, very particularly preferably trifluoromethyl or pentafluoroethyl.

If R is non-fluorinated it is preferably methyl, ethyl, n-butyl, n-hexyl, very particularly preferably methyl or ethyl.

$R^F$ is each independently of another a perfluorinated straight-chain or branched alkyl group having 1 to 6 C atoms. It is preferably trifluoromethyl, pentafluoroethyl or nonafluorobutyl, very particularly preferably trifluoromethyl or pentafluoroethyl.

Examples of anions of organic acids are pyruvate, lactate, acetate, citrate, butyrate, malate, oxalate and/or tartrate.

Preferably the anion is selected from anions of organic acids, halides, nitrates, sulfates, thiosulphates, phosphates, carbonates, sulfonates, hydroxides and carboxylates as described above. For example, the anion may be selected from chloride, acetate, trifluoroacetate, methanesulfonate, glycolate, benzoate, salicylate, (±)-lactate, (+)-lactate, (−)-lactate, (+)-pantothenate, (±)-tartrate, (+)-tartrate, (−)-tartrate, (±)-hydrogen tartrate, (+)-hydrogen tartrate, (−)-hydrogen tartrate, (±)-potassium tartrate, (+)-potassium tartrate, (−)-potassium tartrate, meso-tartrate, meso-1-hydrogen tartrate, meso-2-hydrogen tartrate, meso-1-potassium tartrate, meso-2-potassium tartrate. Another preferred anion is an organic carboxylate.

There are no restrictions per se with respect to the choice of the cation $K^+$ of the ionic liquid. However, preference is given to biocompatible, organic cations such as: ammonium, phosphonium, uronium, thiouronium, guanidinium cations or heterocyclic cations.

Ammonium cations can be described, for example, by the formula (1)

$$[NR_{a4}]^+ \tag{1}$$

where $R_a$ in each case, independently of one another, denotes H, where all substituents $R_a$ cannot simultaneously be H, OR', NR'$_2$, with the proviso that a maximum of one substituent R$_a$ in formula (1) is OR', NR'$_2$, straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more R may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R' may be =H, non-, partially or perfluorinated C$_1$- to C$_6$-alkyl, C$_3$- to C$_7$-cycloalkyl, unsubstituted or substituted phenyl and X may be =halogen.

Phosphonium cations can be described, for example, by the formula (2)

[PR$^2_4$]$^+$    (2), where

R$^2$ in each case, independently of one another, denotes H, OR' or NR'$_2$ straight-chain or branched alkyl having 1-20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more R$^2$ may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R$^2$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated C$_1$- to C$_6$-alkyl, C$_3$- to C$_7$-cycloalkyl, unsubstituted or substituted phenyl and X=halogen.

Uronium cations can be described, for example, by the formula (3)

[(R$^3$R$^4$N)—C(=OR$^5$)(NR$^6$R$^7$)]$^+$    (3), and thiouronium cations by the formula (4),

[(R$^3$R$^4$N)—C(=SR$^5$)(NR$^6$R$^7$)]$^+$    (4), where

R$^3$ to R$^7$ each, independently of one another, denotes hydrogen, where hydrogen is excluded for R$^5$, straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more of the substituents R$^3$ to R$^7$ may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R$^3$ to R$^7$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated C$_1$- to C$_6$-alkyl, C$_3$- to C$_7$-cycloalkyl, unsubstituted or substituted phenyl and X=halogen.

Guanidinium cations can be described by the formula (5)

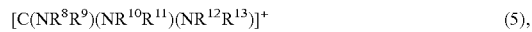

[C(NR$^8$R$^9$)(NR$^{10}$R$^{11}$)(NR$^{12}$R$^{13}$)]$^+$    (5), where

R$^8$ to R$^{13}$ each, independently of one another, denotes hydrogen, —CN, NR'$_2$, —OR' straight-chain or branched alkyl having 1 to 20 C atoms, straight-chain or branched alkenyl having 2-20 C atoms and one or more double bonds, straight-chain or branched alkynyl having 2-20 C atoms and one or more triple bonds, saturated, partially or fully unsaturated cycloalkyl having 3-7 C atoms, which may be substituted by alkyl groups having 1-6 C atoms, where one or more of the substituents R$^8$ to R$^{13}$ may be partially or fully substituted by halogens, in particular —F and/or —Cl, or partially by —OH, —OR', —CN, —C(O)OH, —C(O)NR'$_2$, —SO$_2$NR'$_2$, —C(O)X, —SO$_2$OH, —SO$_2$X, —NO$_2$, and where one or two non-adjacent carbon atoms in R$^8$ to R$^{13}$ which are not in the α-position may be replaced by atoms and/or atom groups selected from the group —O—, —S—, —S(O)—, —SO$_2$—, —SO$_2$O—, —C(O)—, —C(O)O—, —N$^+$R'$_2$—, —P(O)R'O—, —C(O)NR'—, —SO$_2$NR'—, —OP(O)R'O—, —P(O)(NR'$_2$)NR'—, —PR'$_2$=N— or —P(O)R'— where R'=H, non-, partially or perfluorinated C$_1$- to C$_6$-alkyl, C$_3$- to C$_7$-cycloalkyl, unsubstituted or substituted phenyl and X=halogen.

Most preferred are cations composed of a quaternary nitrogen-based ion, preferably based on a nucleus selected from quaternary ammonium cations, hydroxylammonium cations, pyrazolium cations, imidazolium cations, triazolium cations, pyridinium cations, pyridazinium cations, pyrimidinium cations, pyrazinium cations and triazinium cations. The heterocyclic nucleus may be substituted at any carbon or nitrogen atom by any C1-C12 alkyl, alkenyl, alkoxy, alkenedioxy, allyl, aryl, arylalkyl, aryloxy, amino, aminoalkyl, thio, thioalkyl, hydroxyl, hydroxyalkyl, oxoalkyl, carboxyl, carboxyalkyl, haloalkyl or halide function including all salts, ethers, esters, pentavalent nitrogen or phosphorus derivatives or stereoisomers thereof. When required and where possible, any of these functions may include a functional group selected from the group consisting of alkenyl, hydroxyl, amino, thio, carbonyl and carboxyl groups.

Examples of quarternary ammonium cations are choline or betaine and derivatives thereof.

Examples of hydroxylammonium cations are N-alkyl hydroxylammonium ions; N,N-dialkyl hydroxylammonium ions (for instance N,N-dimethyl, N-methyl-N-ethyl, N-methyl-N-propyl, N,N-diethyl, N-ethyl-N-propyl, N,N-dipropyl or N,N-dibutyl hydroxylammonium ions); N,N,N-trialkyl hydroxylammonium ions (for instance N,N,N-trimethyl, N-ethyl-N-methyl-N-propyl, N,N,N-triethyl or N,N,N-tripropyl hydroxylammonium ions); N-alkyl-N-hydroxyalkyl hydroxylammonium ions; N,N-dialkyl-N-hydroxyalkyl hydroxylammonium ions (for instance N,N-dimethyl-N-(2-hydroxyethyl) or N,N-dipropyl-N-(2-hydroxyethyl) hydroxylammonium ions); N-alkyl-O-alkyl hydroxylammonium ions (for instance N-ethyl-O-alkyl or N-alkyl-O-methyl or N-ethyl-O-methyl hydroxylammonium ions); O-alkyl-N,N-dialkyl hydroxylarnmonium ions (for instance O-methyl-N,N-dialkyl, O-.rho.ro.rho.yl-N,N-dialkyl, O-octyl-N,N-dialkyl, O-alkyl-N,N-diethyl or O-alkyl-N,N-dipropyl hydroxylammonium ions); O-alkyl-N,N,N-trialkyl hydroxylammonium ions, in particular O-methyl-N,N,N-trialkyl hydroxylammonium ions (for instance N,N,N,O-tetramethyl or N,N,N-triethyl-O-methyl hydroxylammomum ions); and O-alkyl-N,N-dialkyl-N-hydroxyalkyl hydroxylammonium ions (for instance N,N,O-trimethyl-N-(2-hydroxyethyl), N5N-diethyl-N-(2-hydroxyethyl)-O-methyl or N,N-dipropyl-N-(2-hydroxyethyl)-O-methyl hydroxylammonium ions).

Particularly preferred cations are choline (the N,N,N-trimethylethanolammonium cation) and derivatives and/or trimethylglycine and/or other betaines. Suitable derivatives are for example 2-methyl-choline, ethers and esters of choline such as acetylcholine, lactylcholine, propinoylcholine, buturylcholine, or the methyl-, ethyl-, vinyl- or butyl-ether of choline and esters of betaine, Most preferred is the N,N,N-trimethylethanolammonium cation.

In one embodiment, the ionic liquid may also comprise ectoin or derivatives of ectoin ((S)-1,4,5,6-tetrahydro-2-methyl-4-pyrimidinecarboxylic acid).

Non-toxic, water soluble ionic liquids are for example disclosed in EP 1594974, EP 1805131, WO 2006/038013, WO 2007/036712 and WO 2007/063327.

Deep eutectic solvents are liquids having a melting point that is lower than the melting point of the two or more components that form the eutectic mixture. The components of the deep eutectic solvent (DES) typically interact with each other through hydrogen bond interactions. Examples of deep eutectic solvents are disclosed in WO 2011/15589 and Chem. Soc. Rev., 2012, 41, 7108-7146. Compared to ordinary solvents, deep eutectic solvents have a very low volatility and are typically non-flammable. They share a lot of characteristics with ionic liquids.

Typically deep eutectic solvents can be assigned to 4 groups: type 1 to type 4 DES:

Type I Quaternary ammonium salt+metal chloride

Type II Quaternary ammonium salt+metal chloride hydrate

Type III Quaternary ammonium salt+hydrogen bond donor

Type IV Metal chloride hydrate+hydrogen bond donor

For use in the present invention, type III DES comprising a quarternary ammonium salt and a hydrogen bond donor are especially preferred.

Examples of hydrogen bond donors are alcohols, carboxylic acids, amines, amides like urea, acetamide or thiourea. Examples of alcohols are m-cresol, fructose, glycerol and ethylene glycole.

Examples of quarternary ammonium salts are choline salts, betaine, N-ethyl-2-hydroxy-N, N-dimethylethanaminiumchlorid, ethylammonium chloride, tetrabutylammonium chloride, triethylbenzylammonium chloride and acetylcholine chloride and derivatives thereof, The hydrogen bond donor of the solvents is preferably selected from at least one naturally occurring organic acid, at least one naturally occurring mono- or dimeric sugar, sugar alcohol, amino acid, di or tri alkanol or betaine derivatives.

Said sugar or sugar alcohol may be selected from the group of sucrose, glucose, fructose, lactose, maltose, cellobiose, arabinose, ribose, ribulose, galactose, rhamnose, raffinose, xylose, sucrose, mannose, trehalose, mannitol, sorbitol, inositol, ribitol, galactitol, erythritol, xyletol and adonitol, and, as well as their phosphates.

The said organic acid may be selected from amino acids, malic acid, maleic acid, citric acid, lactic acid, pyruvic acid, fumaric acid, succinic acid, lactic acid, acetic acid, aconitic acid, tartaric acid, malonic acid, ascorbic acid, glucuronic acid, oxalic acid, neuraminic acid and sialic acids.

The DES preferably comprise quaternary ammonium salts like choline or betaine. An example of a DES is a mixture of choline chloride and urea in a 1:2 molar ratio. Other deep eutectic solvents of chorine chloride are formed with malonic acid, citric acid, succinic acid, phenol and glycerol. Examples of DES formed with betaine are mixtures of betaine with urea, malonic acid or citric acid.

Preferably, the DES to be used according to the present invention comprise a quaternary ammonium salt and a carboxylic acid.

Preferably, the DES to be used according to the present invention comprise choline or betaine or derivatives or salts thereof. Suitable derivatives are for example 2-methyl-choline, ethers and esters of choline such as acetylcholine, lactylcholine, propinoylcholine, buturylcholine, or the methyl-, ethyl-, vinyl- or butyl-ether of choline and esters of betaine, Most preferred is choline. Suitable examples are e.g. disclosed in J. Am. Chem. Soc. 2004, 126, 9142-9147. Typically the cholines are present in the form of the chloride or hydroxide.

In another preferred embodiment, the DES comprise an amino acid and/or derivatives thereof. Examples of suitable derivatives are inorganic ester derivatives such as in case of tyrosine and cysteine (S)-2-Amino-3-(4-phosphonooxy-phenyl)-propionic acid or salts thereof and (S)-2-amino-3-sulfosulfanylpropanoic acid or salts thereof.

Most preferred are the amino acids cysteine and/or tyrosine and their derivatives.

In a preferred embodiment, the DES is comprised of choline and/or betaine and/or derivatives or salts thereof and one or more amino acids.

The gist of the present invention is to provide cell culture media that can be stored for a long time (long shelf life), comparably to dry powder cell culture media, and at the same time can be easily dissolved in a suitable solvent to produce cell culture media in shorter time compared to the time necessary to dissolve dry powder media. This is achieved by the addition of one or more components of the medium as part of or dissolved in an Ionic liquid (IL) or a Deep Eutoctic solvent (DES). It has been found that deep eutectic solvents and/or ionic liquids are perfectly suitable as cell culture media components as they are liquids and can be stored comparably to dry powder media. Furthermore, one can choose the composition of the deep eutectic solvents or ionic liquids such that they are formed by at least one component which is required in the cell culture medium. That means, the solvent of the cell culture medium component is not only used as a solvent but is part of the cell culture medium itself.

A liquid is an almost incompressible fluid that conforms to the shape of its container but retains an (almost) constant volume independent of pressure. As such, it is one of the four fundamental states of matter (the others being solid, gas, and plasma), and is the only state with a definite volume but no fixed shape. A liquid is a fluid.

Typically the cell culture medium of the present invention is a cell culture medium composition comprising at least two components. One component is a dry powder cell culture medium. This cell culture medium component comprises all ingredients that can easily be dissolved. For use, the dry powder cell culture medium component is mixed with a suitable solvent like water or a buffer.

The other component of the cell culture medium composition is a liquid cell culture medium component comprising an ionic liquid and/or a DES. This liquid components may comprise such ingredients which are not easily dissolved in sufficient amounts if provided as a dry powder. Such ingredients may be part of the ionic liquid and/or DES or may be dissolved in it.

In one embodiment the liquid cell culture media component is only formed by a deep eutectic solvent or an ionic liquid. A person skilled in the art knows how to make deep eutectic solvents or ionic liquids.

There are various methods to synthesize ionic liquids known to a person skilled in the art. One way of synthesizing ionic liquids is to use a one-way reaction, in which the desired ionic liquids are produced directly from their starting materials. Hereby, the cation and anion are formed together in the same working step.

As an alternative, an ionic liquid can be synthesized via two or more reaction steps. For this, typically, the cation is prepared as a salt with an easily changeable anion such as a halide anion. Afterwards an anion metathesis is performed. Anion metathesis can be realized in various ways in accordance with the available anion source and preference of the method leading to minimal degree of impurities as possible. Processes for the preparation of ionic liquids are described, for example, in P. Wasserscheid, T. Welton (Eds.), Ionic Liquids in Synthesis, Second Edition, WILEY-VCH, Weinheim, 2008.

Deep eutectic solvents can for example be prepared by mixing all components and treat them under elevated temperature. The temperature is dependent on the components. For DES comprising choline, a temperature between 100 and 150° C. is typically suitable. Preferably, the mixture is agitated during heating, e.g. by stirring, shaking etc.

The deep eutectic solvent is formed when the mixture becomes a clear liquid which is free of crystals. Typically, a mixing time between 30 and 60 minutes is suitable.

In case of DES comprising three or more components, it is also possible to form two or more binary mixtures each comprising two components of the envisaged DES and heat them to generate binary DES. The two or more binary DES are then mixed in a second step to form the DES comprising three or more components.

The deep eutectic solvent and/or the ionic liquid can be used directly as liquid cell culture medium component.

The DES and/or ionic liquid can also be used to solubilize further components such as amino acids, saccharides like glucose, metal salts like iron salts, trace elements, vitamins, pluronic, proteins like rBSA, signal molecules like IPTG or insulin or others which are typically needed in cell culture media. Preferably the liquid cell culture medium component comprises such ingredients that cannot be added to the dry cell culture medium component due to e.g. stability or solubility problems.

To modify the viscosity of the liquid cell, culture medium component, a solvent, e.g. water or glycerol, preferably water, can be added. Typically the liquid cell culture medium component does not comprise more than 50% of a solvent such as water (w/w). Preferably, it does not comprise more than 10% (w/w).

In a preferred embodiment, the liquid cell culture medium component comprises choline or betaine. Those components can e.g. be present as a salt. Choline can for example be present as choline hydroxide, choline chloride, choline bicarbonate.

In a preferred embodiment, the liquid cell culture medium component comprises a deep eutectic solvent, preferably a DES comprising choline. In a very preferred embodiment, the liquid cell culture medium component comprises a DES formed at least by choline or a choline (Ch) derivative and an amino acid such as tyrosine (Tyr) or cysteine (Cys) or a derivative.

Preferably, to form a DES comprising tyrosine, this component is added in the form of tyrosine HCl. Preferably, to form a DES comprising cysteine, this component is added in the form of cysteine HCl $H_2O$.

Especially preferred DES are made by or comprise the following mixtures:
  Cys HCl $H_2O$:ChCl, preferably between 0.75:1 and 1:2.5 (w/w)
  Tyr HCl:ChCl:$H_2O$, preferably Tyr HCl and ChCl have a ration between 0.75:3 and 1.5:3 (w/w), most preferred 1:3 and the ratio between water and the mixture of Tyr HCl and ChCl is between 0.75:1 and 3:1, preferably between 3:3 and 3:5 (w/w)
  ChCl:Cys HCl $H_2O$:Tyr HCl:$H_2O$ (e.g. 6:1.5:1:10 (w/w))

The pH of the DES and/or the ionic liquid and thus of the liquid cell culture medium component can be amended by adding suitable buffer components and/or by selection of the ingredients and their specific salt forms, e.g. choline chloride versus choline hydroxide.

The cell culture medium composition of the present invention is typically provided as kit of parts comprising at least the dry cell culture medium component and the liquid cell culture medium component comprising an ionic liquid and/or a DES.

For use in cell culture, the cell culture medium composition of the present invention is typically dissolved in a suitable solvent like water or a buffer and mixed with the cells to be cultures.

In a preferred embodiment, the cell culture medium composition of the present invention is a base medium that is used to start the cell culture process.

In another embodiment, the cell culture medium composition of the present invention is added to the cell culture at a later stage and in addition to the base medium used to start the cell culture. In this case, it is used as a feed medium.

The present invention is thus further directed to a process for cell culture comprising the following steps:
  a) Providing a bioreactor and a cell culture medium composition comprising a dry cell culture medium component and a liquid cell culture medium component which comprises an ionic liquid and/or a deep eutectic solvent
  b) Dissolving the cell culture media composition in a solvent to generate a liquid cell culture medium
  c) Adding to the bioreactor the liquid cell culture medium of step b) either as a base medium to start cell culture to which the cells to be cultured are added afterwards or as a feed medium which is added to the cells which are already present in the bioreactor in a liquid cell culture medium
  d) Performing a cell culture in said bioreactor.

Performing a cell culture is known to a person skilled in the art. This is typically done by incubating the cells under suitable conditions like pH, osmolality, temperature, agitation, aeration (oxygen/$CO_2$) etc. and the optional addition of feed media one or several times during the cell culture. Preferably, the cell culture is performed as fed-batch cell culture.

Fed-batch culture is a cell culture process where one or more nutrients (substrates) are fed (supplied) to the bioreactor during cultivation of the cells and in which the product(s) remain in the bioreactor until the end of the run. An alternative description of the method is that of a culture in which a base medium supports the initial cell culture and a feed medium is added to prevent nutrient depletion. The advantage of the fed-batch culture is that one can control concentration of fed-substrate in the culture liquid at arbitrarily desired levels.

Generally speaking, fed-batch culture is superior to conventional batch culture when controlling concentrations of a nutrient (or nutrients) affect the yield or productivity of the desired metabolite.

In one embodiment, the liquid cell culture medium component comprises amino acids, preferably cysteine and/or tyrosine.

In another embodiment, the liquid cell culture medium component comprises other components which are not part of the ionic liquid or deep eutectic solvent which are dissolved in the ionic liquid and/or deep eutectic solvent.

In one embodiment, the cells in the bioreactor are stem cells, eukaryotic cells, prokaryotic cells, yeasts, fungi, insect cells or algae.

In one embodiment, the liquid cell culture medium component provided in step a) as part of the cell culture medium composition comprises less than 50% (w/w), preferably less than 10% of water.

Preferably, the pH of the liquid cell culture medium component provided in step a) as part of the cell culture medium composition is between pH 5 and 9, most preferred between pH 6 and 8.

In a preferred embodiment, also the feed media that are added to the cell culture comprise a DES and/or an ionic liquid. Depending on the protocol of the cell culture, additional liquid feed is added one or several times in the course of the culture process. The composition of the liquid feed medium that is added can be identical each time it is added or different.

The present invention is further directed to the use of a cell culture medium composition according to the present invention as a nutrient feed and/or as an osmolarity modulator and/or as a pH regulator and/or to support growth of cells and/or to support the production of target molecules. Depending on the composition of the medium composition one or several of the above mentioned effects can be reached by adding the medium composition according to the present invention to a cell culture.

The cell culture medium composition of the invention and the process of the present invention offer an alternative to the use of only dry cell culture media. The cell culture medium composition of the present invention combines a high concentration with excellent dissolution properties. For the first time, highly concentrated media can be used for cell culture without dissolution problems. The volume of the cell culture is kept as low as possible without causing dilution by the addition of large volumes of a solvent. This leads to a cell culture with efficient cell growth, the cells can be kept at the desired optimal physiological state. Process parameters such as product yield, process speed and space/time consumption can be optimized. The cell culture process can be kept very stable and defined, e.g. as it is not necessary to add tyrosine and/or cysteine in a large solvent volume and/or at basic pH.

It is possible to take one or several desired components, such as amino acids, with high melting points, for example cysteine or tyrosine, and which are not very soluble under standard conditions in biologically compatible solvents, for example water, and nevertheless to make a liquid containing nearly 50% amino acid by contacting them with at least a second solid, for example choline chloride.

Such mixtures can be further contacted with other components (solids, liquids or gases) in order to tune the properties of the mixture and to make it more desirable for its intended use. For example the physicochemical properties such as the viscosity of the deep eutectic solvent and/or an ionic liquid can be optimized by the addition of small amounts of water. Thus, such mixtures may comprise between 10% and 100% DES.

The components of the deep eutectic solvent and/or an ionic liquid are selected from compounds that do not cause negative effects on the cellular growth. The non-toxic compounds choline and betaine are ideal in this respect.

The present invention is further illustrated by the following figures and examples, however, without being restricted thereto.

The entire disclosure of all applications, patents, and publications cited above and below, as well as of corresponding European patent application EP 15001613.7, filed on May 29, 2015, are hereby incorporated by reference.

EXAMPLES

Comparison of Dissolution Time

The dissolution time of a dry powder tyrosine HCl shall be compared with the dissolution time of a DES comprising Tyrosine HCl. The final concentration of tyrosine in the resulting liquid is set with 0.26 g/L.

Procedure:

A stirrer tank (280 rpm) at 37° C. is filled with 800 ml of a 100 mM HEPES buffer, the pH is adjusted to pH 7 with 2 mol/l NaOH and then the tyrosine sample (powder or DES) is poured onto the surface of the buffer solution.

DES: Tyr HCl:ChCl (1:3), 0.79 g

Powder: a powder mixture of 0.208 g Tyr HCl and 0.36 g ChCl

Focused Beam Reflectance Measurement-Sensor

Mettler Toledo G400

Software: iC FBRM™ 4.3

FIGS. 1 to 5 show the dissolution of the dry powder and the DES respectively. The x-axis shows the time in all Figures.

A comparison of FIGS. 1 and 2 shows that in case of the DES (FIG. 2), almost no particles or disturbance can be detected in the mixture and complete dissolution is reached after about 10 minutes, whereas in case of the powder (FIG. 1), dissolution takes about 1 hour or more.

The same can also be seen from FIGS. 3 to 5 which show the same measurement in more detail. FIG. 3 is directed to the change of particle number over the time. FIGS. 4 and 5 show the content of particle of different sizes in solution over time.

BRIEF DESCRIPTION OF DRAWINGS

FIG. 1 shows a comparison between the dissolution of a dry powder tyrosine HCl sample and a DES comprising tyrosine HCl.

FIG. 2 shows a comparison between the dissolution of a dry powder tyrosine HCl sample and a DES comprising tyrosine HCl.

Figure 3A:
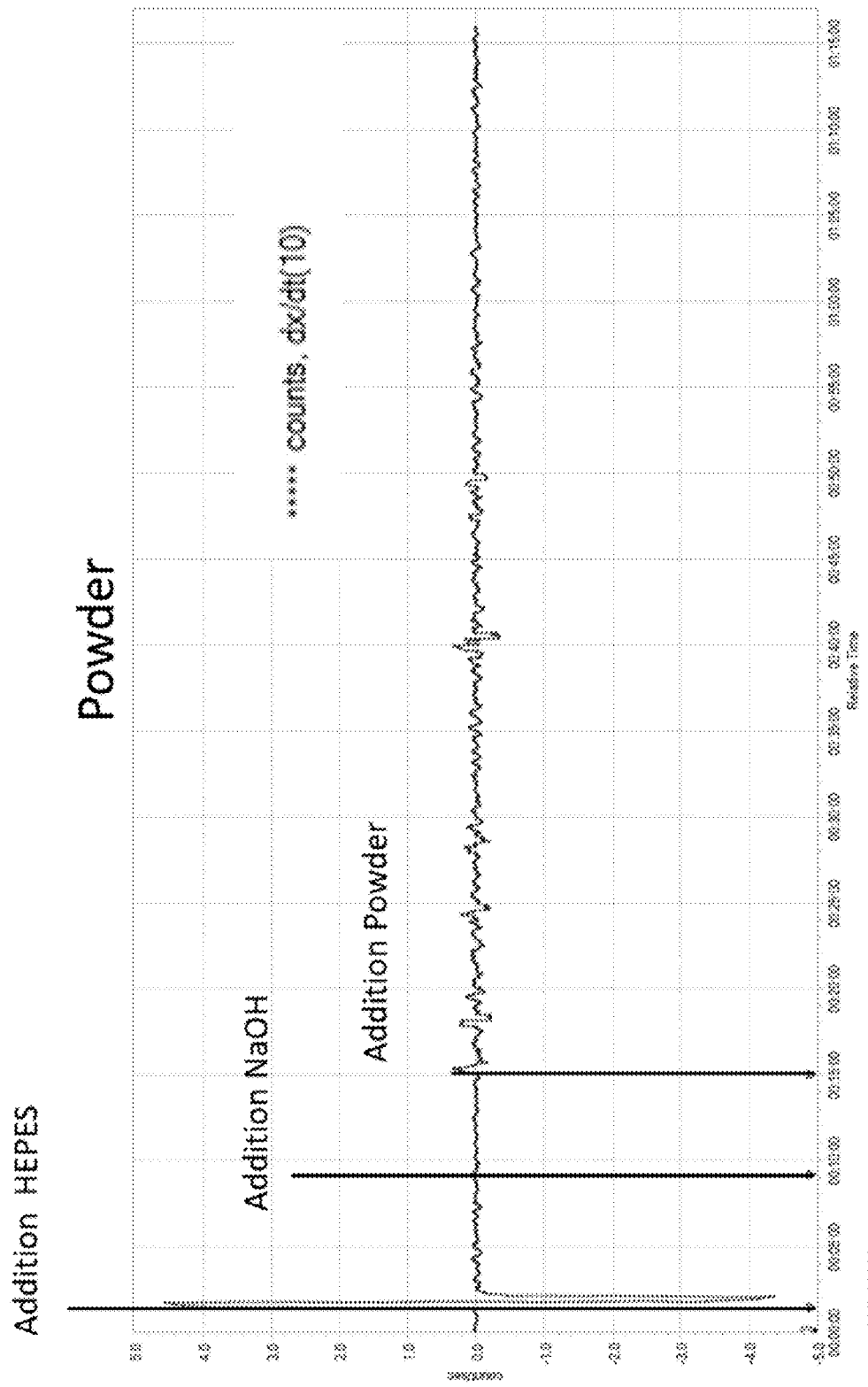
FIG. 3A shows the dissolution of a dry powder tyrosine HCl sample.
Figure 3B:
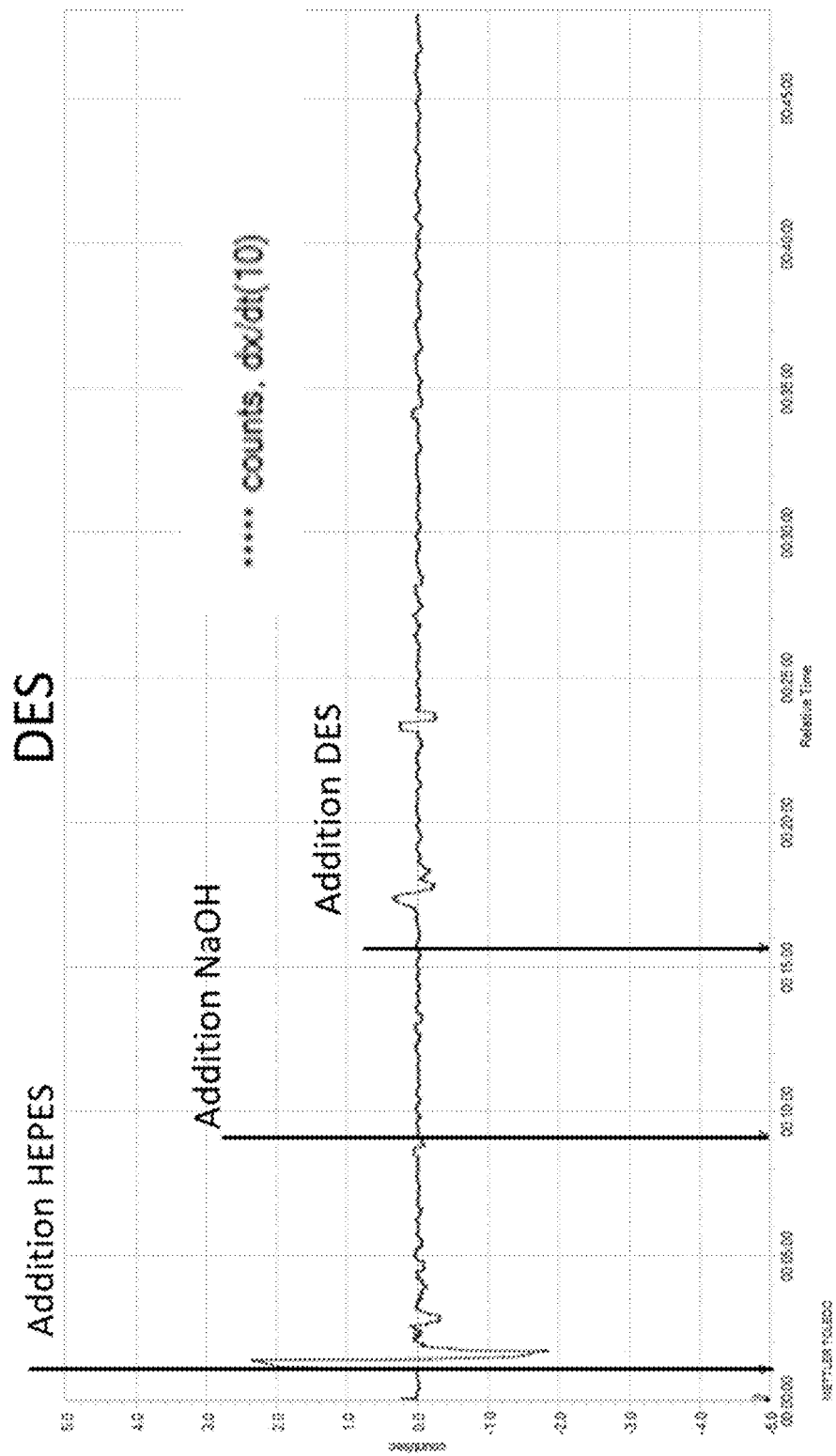
FIG. 3B shows the dissolution of a DES comprising tyrosine HCl.
Figure 4:
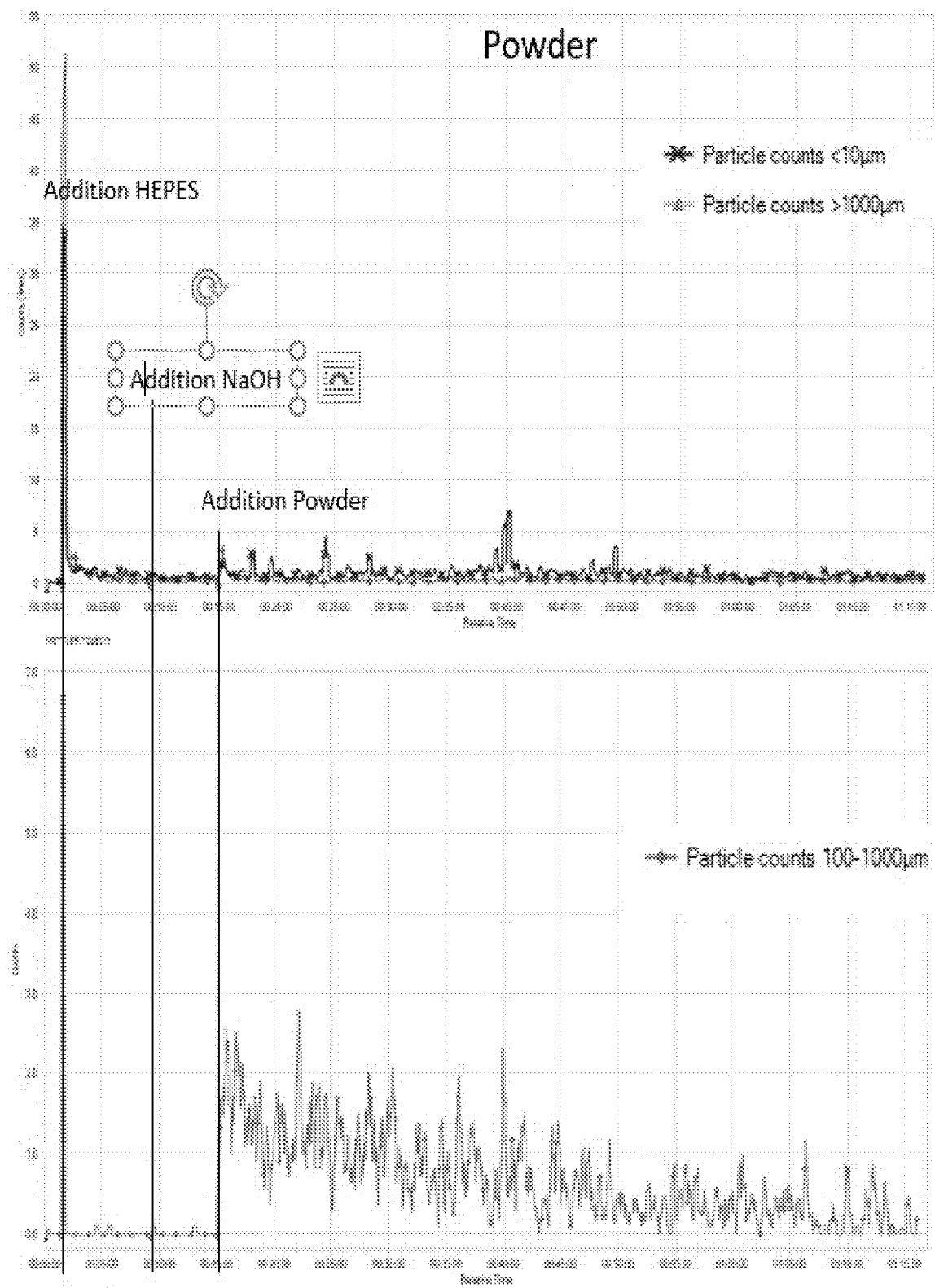
FIG. 4 shows a comparison between the dissolution of a dry powder tyrosine HCl sample and a DES comprising tyrosine HCl.
Figure 5:
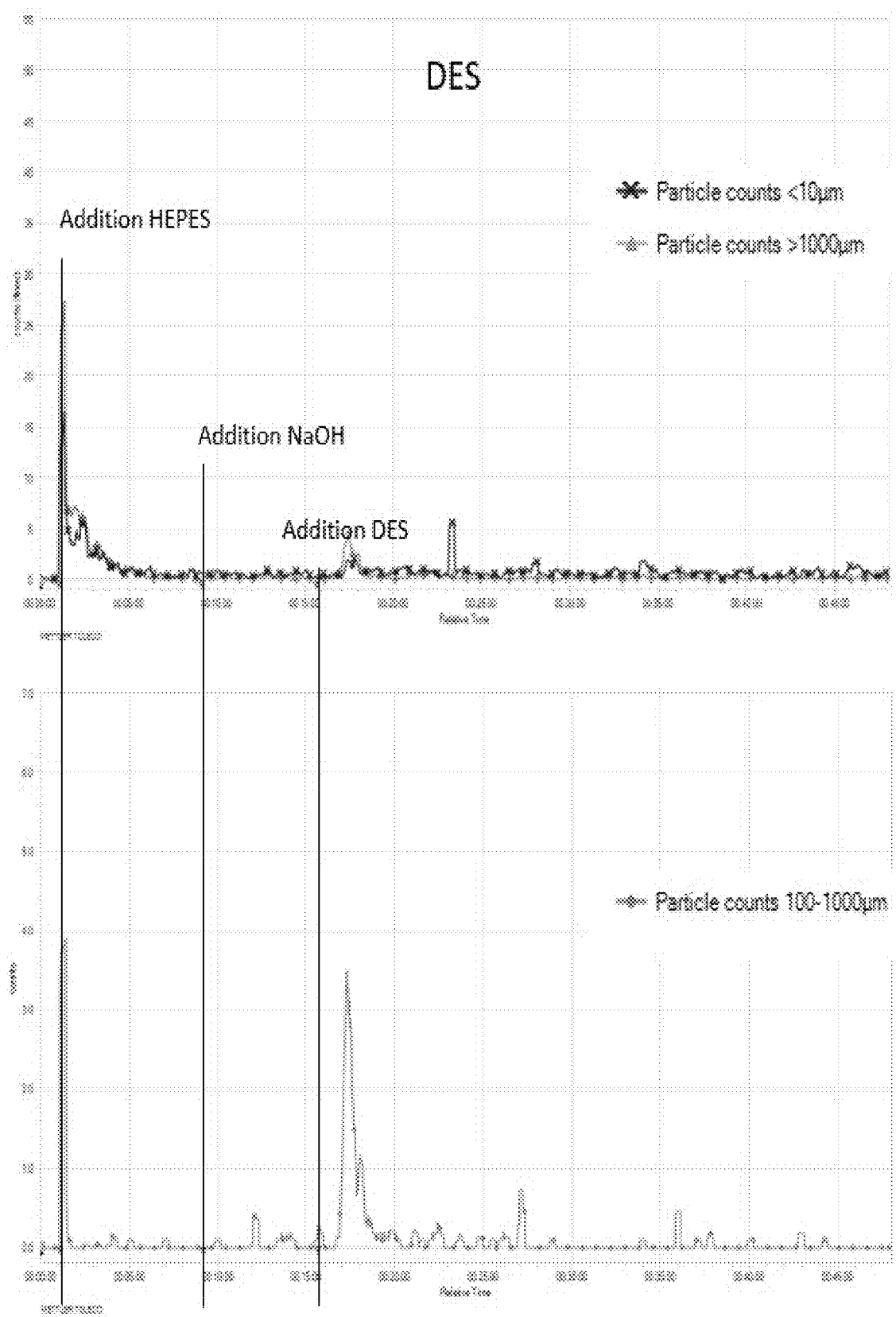
FIG. 5 shows a comparison between the dissolution of a dry powder tyrosine HCl sample and a DES comprising tyrosine HCl.

The invention claimed is:

1. A cell culture medium kit, comprising, in said kit separately, a dry powder cell culture medium component and a liquid cell culture medium component which are both used to form a composition, wherein the liquid cell culture medium component comprises a deep eutectic solvent comprising choline and/or betaine and/or a derivative or salt thereof and one or more amino acids, and wherein the deep eutectic solvent does not comprise more than 50% water based on weight.

2. The cell culture medium kit according to claim 1, wherein the composition is a base medium or a feed medium.

3. The cell culture medium kit according to claim 1, wherein the liquid cell culture medium component is liquid at or below 35° C.

4. The cell culture medium kit according to claim 1, wherein the liquid cell culture medium component comprises choline and/or betaine or a salt thereof.

5. The cell culture medium kit according to claim 1, wherein the liquid cell culture medium component comprises a quaternary ammonium salt.

6. The cell culture medium kit according to claim 1, wherein the liquid cell culture medium component comprises choline and betaine.

7. The cell culture medium kit according to claim 1, wherein the liquid cell culture medium component comprises cysteine and/or tyrosine.

8. The cell culture medium kit according to claim 1, wherein the liquid cell culture medium component comprises ingredients which are not part of the deep eutectic solvent and which are dissolved in the deep eutectic solvent.

9. The cell culture medium kit according to claim 1, wherein the deep eutectic solvent does not comprise more than 10% water based on weight.

10. A process for cell culture, comprising:
mixing the composition from the cell culture medium kit according to claim 1 with water or with a composition containing water, and adding the resultant composition to a bioreactor either as a base medium to which cells are added afterwards to start a cell culture or as a feed medium to a cell culture already present in the bioreactor.

11. The process for cell culture according to claim 10, wherein the liquid cell culture medium component is liquid at a temperature between 20 and 35° C.

12. The process for cell culture according to claim 10, wherein the liquid cell culture medium component comprises cysteine and/or tyrosine.

13. The process for cell culture according to claim 10, wherein the cells in to the bioreactor are stem cells, eukaryotic cells, prokaryotic cells, archaea, bacteria, yeasts, fungi, insect cells or algae.

14. The process for cell culture according to claim 10, wherein the liquid cell culture medium component comprises less than 10% of water.

15. A cell culture medium, comprising a composition that has been formed from a dry powder cell culture medium component and a liquid cell culture medium component, wherein the liquid cell culture medium component comprises a deep eutectic solvent comprising choline and/or betaine and/or a derivative or salt thereof and one or more amino acids, and wherein the deep eutectic solvent does not comprise more than 50% water based on weight.

16. The cell culture medium according to claim 15, wherein the deep eutectic solvent does not comprise more than 10% water based on weight.

17. The cell culture medium according to claim 15, which comprises
choline and/or betaine or a salt thereof; and/or
a quaternary ammonium salt; and/or
cysteine and/or tyrosine.

* * * * *